United States Patent [19]

Ogawa et al.

[11] Patent Number: 4,576,368
[45] Date of Patent: Mar. 18, 1986

[54] TABLE MECHANISM

[75] Inventors: Yoshiyuki Ogawa; Hideaki Uno; Misao Baba, all of Tokyo, Japan

[73] Assignee: Yokogawa Medical Systems, Limited, Toyko, Japan

[21] Appl. No.: 587,138

[22] Filed: Mar. 7, 1984

[30] Foreign Application Priority Data

Dec. 9, 1983 [JP] Japan .................. 58-233317

[51] Int. Cl.⁴ .................................. A61G 13/00
[52] U.S. Cl. ........................... 269/322; 378/17
[58] Field of Search ............. 269/323, 324, 325, 322; 378/17, 20; 312/210, 297; 254/10 C; 160/148

[56] References Cited

U.S. PATENT DOCUMENTS

| | | | |
|---|---|---|---|
| 835,701 | 11/1906 | Burford | 312/297 |
| 2,922,533 | 1/1960 | La Barge, Jr. | 254/10 C |
| 3,806,109 | 4/1974 | Weber et al. | 269/323 |
| 3,868,103 | 2/1975 | Pageot et al. | 269/325 |
| 4,475,072 | 10/1984 | Schwehr et al. | 269/323 |

Primary Examiner—Frederick R. Schmidt
Assistant Examiner—Judy J. Hartman
Attorney, Agent, or Firm—Moonray Kojima

[57] ABSTRACT

A table mechanism suitable for use in a tomographic system, such as an X-ray computerized tomograph, has a table movable upwardly and downwardly by a parallel link mechanism. The distance of horizontal movement of a cradle on the table can be automatically compensated for, dependent on an angle of angular movement of the parallel link mechanism, while holding the cradle and a gantry, relatively positioned in a constant relation. A side of the parallel link mechanism is covered with a cover mechanism having a relatively small area.

8 Claims, 9 Drawing Figures

(Cradle Position Compensation)

TABLE MECHANISM

BACKGROUND OF THE INVENTION

1. Field of the Invention

This invention relates to a table mechanism, and more particularly to a table mechanism suitable for use in a tomographic system, such as an X-ray computerized tomograph.

2. Description of Prior Art

It is preferable that the table mechanism used in a tomographic system such as an X-ray computerized tomograph, be movable up and down to allow a patient to get on and off the table with ease.

FIG. 1 illustrates a conventional table mechanism comprising a gantry 10, a table 20 having a tabletop 30, and an auxiliary table 40 located remotely from table 20 across gantry 10.

Table 20 comprises a support 21 and a carrier 22 which is movable up and down with respect to a support 21. Table 20 is fixedly positioned in spaced relation to gantry 10. Tabletop 30 is mounted on carrier 22, and comprises a body 31 and a cradle 32 which can be fed from body 31 toward gantry 10. The distal end of cradle 32, as it is fed from body 31, is supported by auxiliary table 40 (as shown by dotted lines). In operation, a patient lies on and is fastened to cradle 32 by a safety belt.

With the conventional construction, since table 20 is fixedly located at a certain distance from gantry 10, working space available between table 20 and gantry 10 is limited. Thus, it takes a considerable amount of time for an operator to position a patient on cradle 32. It is also difficult to lower the initial height of table 20, so that a footstool is necessary to enable the patient to climb on or get off cradle 32.

Thus, there is need for a more convenient and versatile table mechanism for use in the medical field, for example.

SUMMARY OF THE INVENTION

Accordingly, an object of the invention is to overcome the aforementioned and other deficiencies and disadvantages of the prior art.

Another object is to provide a table mechanism which can provide a relatively wide working space between the table and the gantry and which can be readily controlled to lower the initial height of the table.

A further object is to provide a table mechanism wherein the distance of movement of the cradle can automatically be adjusted in response to ascending and descending movement of the table.

A still further object is to provide a table mechanism including a lifting and lowering mechanism which is covered on its side with a cover mechanism having a relatively small area.

The foregoing and other objects are attained by the invention which encompasses a novel table mechanism comprising a table having a tabletop and a cradle mounted on the tabletop for movement parallel thereto; a parallel link mechanism having one end pivotally mounted on the table and an opposite end pivotally mounted on a floor and supporting the table to move the table parallel to the floor; a driving mechanism having one end pivotally mounted on the floor and an opposite end pivotally mounted on a portion of the parallel link mechanism for causing the latter to move the table parallel to the floor; an angle detecting mechanism for detecting an angle of angular movement of the parallel link mechanism; and a control system for controlling the distance of movement of the cradle, based on an output signal from the angle detecting mechanism. Advantageously, the invention enables adjustment of the initial height of the cradle, and simple, versatile up-down movement of the cradle whereby the patient can be placed on the cradle without any stepping stool and then moved upward and then toward the gantry.

DETAILED DESCRIPTION OF PREFERRED EMBODIMENTS

Figure 1:
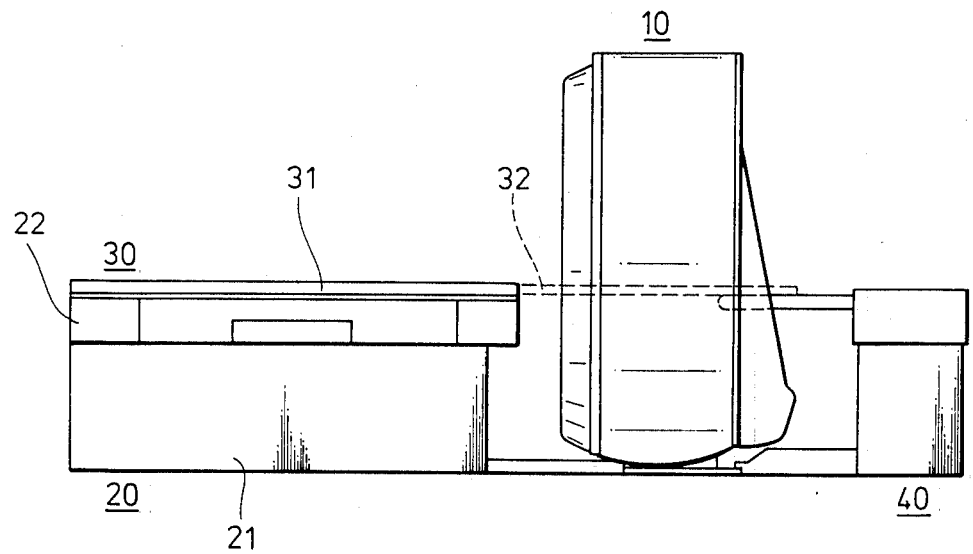
FIG. 1 is a side elevational view of a conventional table mechanism.
Figure 2:
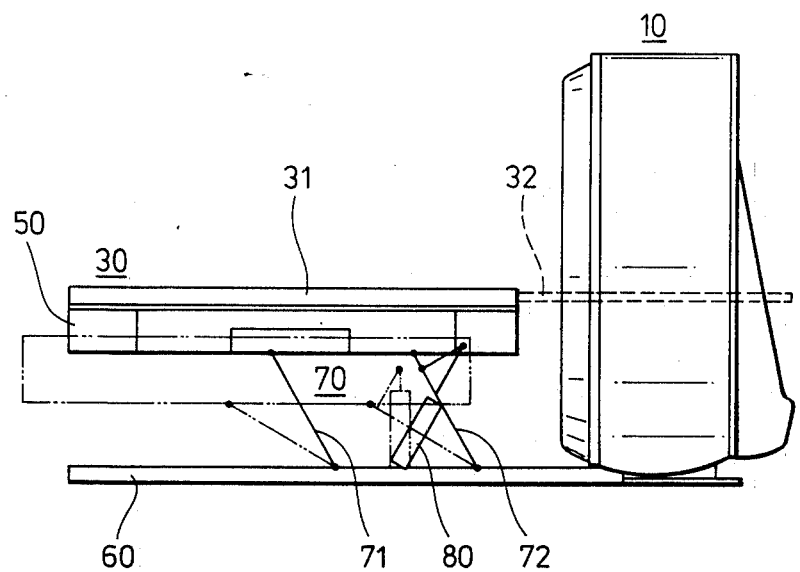
FIG. 2 is a side elevational view depicting an illustrative embodiment of the invention.

FIG. 2 depicts a table mechanism according to the invention. Similar or corresponding parts in FIG. 2 are denoted by similar or corresponding reference characters in FIG. 1.

The illustrative table mechanism of the invention comprises a table 50, a floor 60, a parallel link mechanism 70, a driving mechanism 80, an angle detecting mechanism 90 (see FIG. 3), and a control system (see FIG. 3) 100.

Parallel link mechanism 70 comprises a pair of links 71, 72. Links 71, 72 have ends pivotally connected to table 50 and opposite ends pivotally connected to floor 60. Table 50 is thus supported on links 71, 72 so as to be movable parallel to the floor. Driving mechanism 80 causes parallel link mechanism 70 to move table 50 parallel to floor 60. Driving mechanism 80 has one end pivotally mounted on a portion of parallel link mechanism 70 and an opposite end pivotally mounted on floor 60. Driving mechanism 80 may comprise a hydraulic cylinder mechanism, or a ball screw mechanism, or the like. Angle detecting mechanism 90 serves to detect the angle (see FIG. 3) of swinging movement of parallel link mechanism 70, and may comprise a combination of a gear mechanism and a potentiometer.

Control system 100 (see FIG. 3) serves to control the distance of movement cradle 32 in response to an output signal from angle detecting mechanism 90. Control system 100 comprises an amplifier 101 for amplifying an output signal from angle detecting mechanism 90; an A/D converter 102 for converting an analog output signal from amplifier 101 into a digital signal; a processing unit 103 for dividing angle information represented by the digital signal into positional information in a horizontal direction x and positional information in a vertical direction y to determine the distances of movement in the horizontal and vertical directions, and for generating a control signal to move cradle 32 in an opposite direction by a distance equal to the distance the cradle has moved in the horizontal direction x; and a motor driver 104 for driving a motor 33, to move cradle 32 in response to the control signal from processing unit 103. The height of table 50 can be determined from the output signal from angle detecting mechanism 90, but no arrangement for such height determination is illustrated here for sake of simplicity of description.

The operation of the illustrative table mechanism will now be described. Prior to operation, the table mechanism is in its initial position, as shown by two dot and dash lines in FIG. 2. In the initial position, the driving mechanism 80 is substantially perpendicular to floor 60 and parallel link mechanism 70 is inclined closely to floor 60. The initial height of table 50 may be selected to be about, for example, 500 mm, which is considerably lower than possible with the conventional table mechanism. Accordingly, no footstool is required for the patient to get on or off cradle 32. In the initial position, table 50 is also more widely spaced from gantry 10 than it is in the prior table mechanism, so that a wide working space is available between gantry 10 and table 50, which advantageously, enables the patient on cradle 32 to be positioned quickly and efficiently.

After the patient has been fastened to cradle 32, driving mechanism 80 is turned toward gantry 10 and extended. In response to the turning and extending movement of driving mechanism 80, table 50 is lifted up, while being kept parallel to floor 60, thus approaching gantry 10. After table 50 has been raised to a prescribed height (for example, 800 mm) which is high enough to take tomograms of the patient, cradle 32 is moved toward gantry 10. The distance gantry 10 and table 50, after the latter has been lifted to the prescribed height, is shown in FIG. 2 as being equal to the corresponding distance shown in FIG. 1. However, such distance may be smaller or larger than shown.

After crade 32 has been moved toward and positioned relatively to gantry 10, tomograms are taken of the patient who is positioned on cradle 32, while adjusting the height of the table 50 in an effective height range (e.g. 800 mm-1,000 mm) by turning parallel link mechanism 70. At this time, it is necessary that cradle 32 and gantry 10 be held in a constant position relative to each other, regardless of the height of table 50. According to the invention, such a requirement can be met by controlling the distance of movement of cradle 32 to hold crade 32 and gantry 10 in a desired relative position regardless of the height of table 50, in the following manner to be described.

Figure 4:
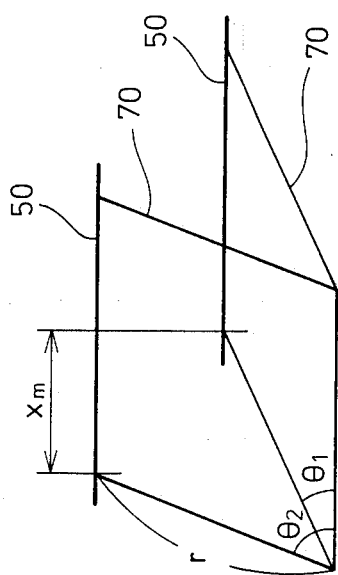
FIG. 4 is a schematic diagram showing operation of the embodiment of FIG. 2.

FIG. 4 is an equivalent representation of the relationship between the angular movement of parallel link mechanism 70 and the movement of table 50 in the horizontal direction x. If parallel link mechanism 70 is angularly moved from an angle $\theta_1$ to an angle $\theta_2$, then a distance xm that table 50 has moved in the direction x can be determined by the following equation:

$$xm = r \cdot \cos \theta_1 - r \cdot \cos \theta_2$$

wherein r is the length of each link. Since length r is constant and known, values of r·cos θ for angles θ can be tabulated and stored. By moving cradle 32 a distance equal to distance xm in a direction opposite to the direction in which table 50 has moved, cradle 32 and gantry 10 can be kept in a constant mutual and relative position, irrespective of how high table 50 may lie.

Figure 3:
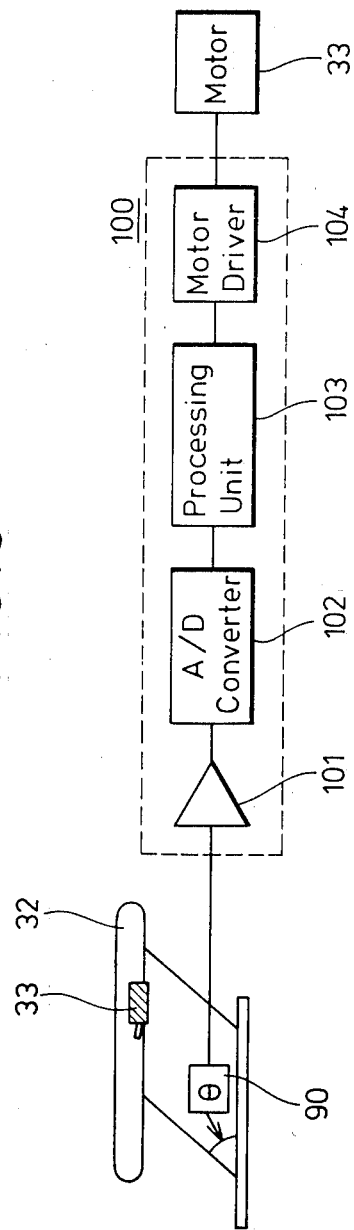
FIG. 3 is a block diagram of a control system for the embodiment of FIG. 2.
Figure 5:
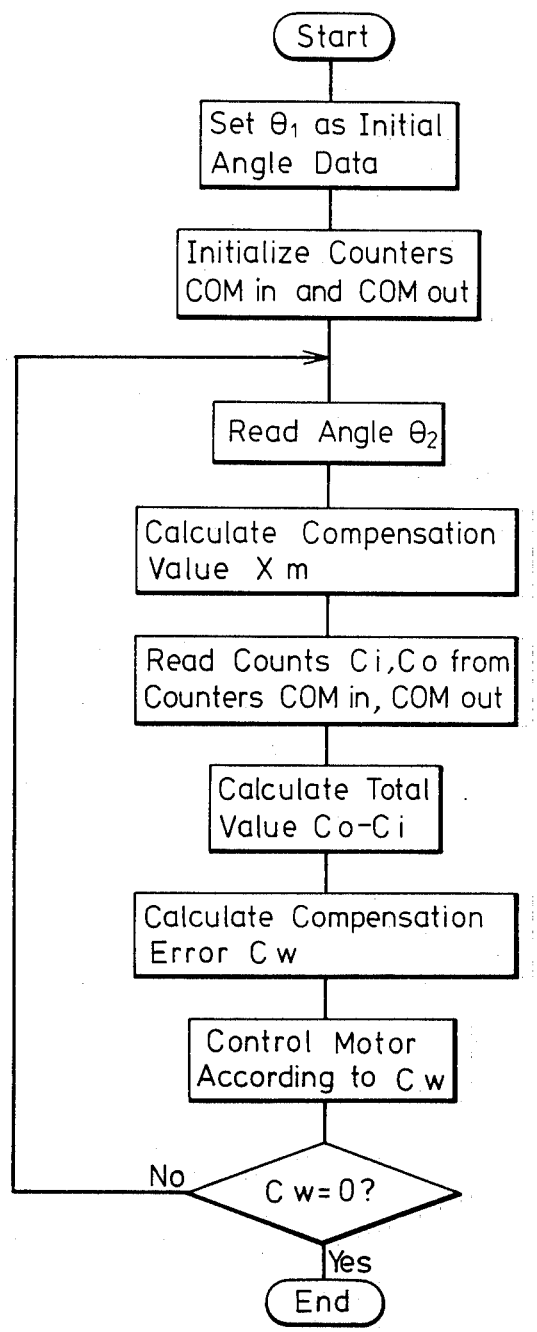
FIG. 5 is a flow chart showing a routine for positional control of the embodiment of FIG. 2.

FIG. 5 is a flow chart of successive steps of position control of cradle 32, effected by the arrangement shown in FIG. 3. The processing unit 102 in control system 100 first sets an angle $\theta_1$ of parallel link mechanism 70 as an initial angle data at the time of start of height adjustment of table 50, to pick up positional data $f(\theta_1)$ of table 50 in direction x. Then, the processing unit 103 initializes counters COMin, COMout which count compensation distances that cradle 32 moves. When parallel link mechanism 70 starts being angularly moved, motor 33 is actuated to move crade 32, at a prescribed speed in a direction opposite to the direction in which table 50 is moved.

The distance of movement of cradle 32 is counted by counter COMin or COMout dependent on the direction in which cradle 32 moves. These counters COMin, COMout, are provided in view of the fact that positional compensation of cradle 32 is more time consuming than is the movement of table 50 due to angular movement of parallel link mechanism 70. The counter COMin counts the distance of movement of cradle 32 toward gantry 10, and the counter COMout counts the distance of movement of cradle 32 away from gantry 10. Then, control system 100 reads an angle $\theta_2$ of angular movement of parallel link mechanism 70 at the time table 50 is adjusted to a desired height, finds positional data $f(\theta_2)$ of table 50 in direction x based on angle $\theta_2$, and calculates xm according to the following equation:

$$xm = f(\theta_1) - f(\theta_2).$$

At this time, processing unit 102 also reads counts Ci, Co from counters COMin, COMout, respectively: calculates a total value co−ci; and also calculates a compensation error Cw according to the following equation:

$$Cw = f(\theta_1) - f(\theta_2) - (Co - Ci).$$

Based on the absolute value and sign of the compensation error Cw thus calculated, the processing unit 103 then issues a control signal to motor driver 104 for energizing motor 33 to move cradle 32 at a prescribed speed in a prescribed direction. The positional compensation for cradle 32 is completed when the compensation error Cw is 0.

For controlling the upward and downward movement of table 50, a manual switch may be attached to table 50 and a foot switch may be mounted on floor 60. Cradle 32 may then be subjected to positional compensation when table 50 is moved upward or downward by use of a manual switch. On the other hand, cradle 32 could be moved upward or downward by use of a foot switch without having any positional compensation. The positioning of the table 50 can then be efficiently and versatilely carried out by selectively using these switches.

Figure 6:
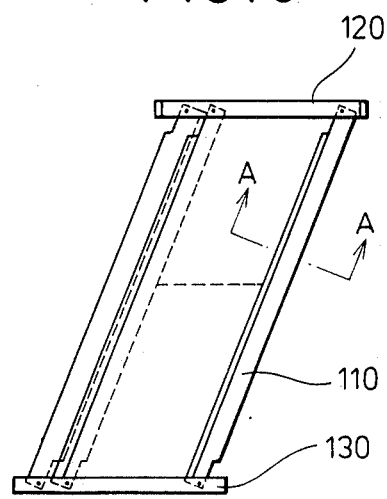
FIG. 6 is a side elevational view depicting a cover mechanism for use with the embodiment of FIG. 2.
Figure 7:
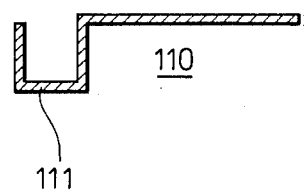
FIG. 7 is a cross-sectional view taken along line A—A of FIG. 6.

FIG. 6 shows a cover mechanism for covering a side of parallel link mechanism 70. The cover mechanism has a plurality of parallel cover members 110 and a pair of attachment plates, 120, 130 to which the ends of cover members 110 are attached. Each of the cover members 110 is of a length substantially equal to that of links 71 and 72, and has a hook-shaped cross section, as shown in FIG. 7, including a U-shaped portion 111 for providing reinforcement against flexing and for providing a decorative effect. In FIG. 6, attachment plate 120 is attached to table 50 and attachment plate 130 is mounted on floor 60. The ends of cover members 110 are pivotally attached to and disposed between attachment plates 120, 130 such that any adjacent ones of cover members 110 will overlap each other at all times to cover the side of the parallel link mechanism 70 regardless of what angular position parallel link mechanism 70 may be located in.

Figure 8A:
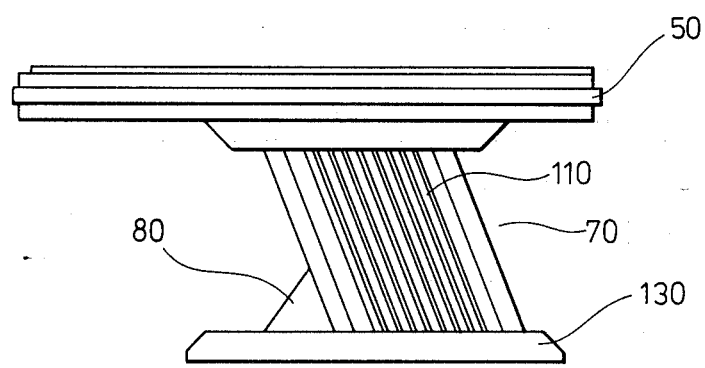
FIGS. 8(A) and 8(B) are side elevational views illustrative of operation of the cover mechanism of FIG. 6.
Figure 8B:
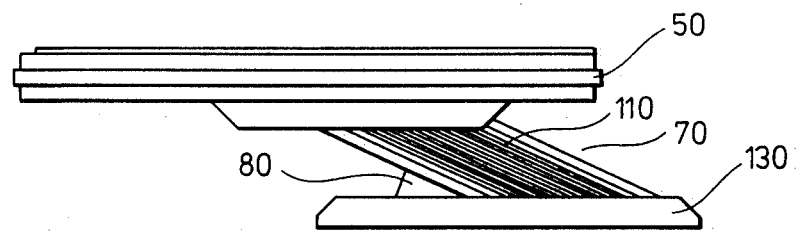

With this arrangement, cover members 110 are angularly moved parallel to each other as parallel link mechanism 70 is angularly moved, as shown in FIGS. 8(A) and 8(B). FIG. 8(A) shows the position of cover members 110 when table 50 is lifted. FIG. 8(B) shows the position of cover members 110 when table 50 is lowered. In FIGS. 8(A) and 8(B), driving mechanism 80 is attached to link 71.

The cover mechanism is smaller in size than other priorly known cover arrangments, such as a bellows like tubular body and a box enclosing the parallel link mechanism, in its entirety. Hence, advantageously, the present covering arrangement has a relatively small area covering the parallel link mechanism.

Each of cover members 110 may be made of molded synthetic resin, bent web of metal, etc.

While the table mechanism is used in an X-ray computerized tomograph, the invention can also be used in other applications.

While no auxiliary table is used in the present embodiment, an auxiliary table may be used, as desired, which can be variable in height and in synchronism with the variation in height of the main table.

The described embodiment has good controllability, is versatile and simple in construction and operation. It also has the following advantages. A relatively wide working space is available between the table and the gantry. The initial height of the table can be readily adjusted, for example, can be readily lowered. Also, the distance of movement of the cradle can be automatically adjusted in response to upward and downward movement of the table. Furthermore, the side of the table lifting and lowering mechanism or the parallel link mechanism, can be covered with a novel cover mechanism which has a relatively small area.

The foregoing description is illustrative of the principles of the invention. Numerous modifications and extensions thereof would be apparent to the worker skilled in the art. All such modifications and extensions are to be considered to be within the spirit and scope of the invention.

What is claimed is:

1. A table mechanism usable in medical diagnostic systems, said table mechanism comprising
    a table resting on a floor and comprising a table top, and a cradle movably mounted on said table top, said cradle having space for holding a patient longitudinally thereon, and wherein at one longitudinal end of said table is defined a work space, both said table top and said cradle being movable into said work space;
    table top lifting means for concurrently moving said table top vertically and horizontally while maintaining said table top parallel to said floor, said moving of said table top being from a rest position near said floor and most distant from said work space to a work position different from said rest position and closest to and into said work space;
    cradle moving means for moving said cradle from a rest position on said table top to a position extended from said table top and into said work space;
    wherein said table top lifting means comprises a parallel link mechanism and a driving mechanism, said driving mechanism being expandable and contractable to drive said parallel link mechanism to cause concurrent vertical and horizontal movement of said table top while maintaining said table top parallel to said floor;
    wherein said parallel link mechanism comprises a plurality of links of substantially the same length and spaced parallel to each other at a predetermined distance from each other, one end of each link being rotatably connected to said table to be angularly movable relative to said table without any lateral movement relative to said table, another end of each link being rotatably connected to said floor to be angularly movable relative to said floor without any lateral movement relative to said floor; and
    wherein said driving mechanism has one end pivotally connected to a portion of said parallel link mechanism and another end pivotally connected to said floor, whereby said driving mechanism fully contracts to move said links of said parallel link mechanism downwardly to a position closest to said floor and consequently moves said table top to said rest position most distant from said work space, and fully expands to move said one ends of said links of said parallel link mechanism upwardly to a position away from said floor, and consequently moves said table top to said work position closest to and into said work space.

2. The table mechanism of claim 1, wherein said driving mechanism of said table lifting means is hydraulically operated mechanism.

3. The table mechanism of claim 1, wherein said driving mechanism of said table lifting means is a ball and screw mechanism.

4. The table mechanism of claim 1, wherein said table lifting means comprises a cover mechanism comprising a plurality of plates disposed outside of said parallel link mechanism and parallel to said links and longitudinally of said table, one end of each plate being pivotally mounted on said table, another end of each plate being pivotally mounted on said floor, adjacent ones of said plates partially and laterally overlapping each other along their entire length.

5. The table mechanism of claim 4, wherein each of said plates of said cover mechanism has a protrusion of U-shaped cross section over an entire non-overlapping portion.

6. A table mechanism usuable in medical diagnostic systems, said table mechanism comprising
    a table resting on a floor and comprising a table top, and a cradle movably mounted on said table top, said cradle having space for holding a patient longitudinally thereon, and wherein at one longitudinal end of said table is defined a work space, both said table top and said cradle being movable into said work space;
    table top lifting means for concurrently moving said table top vertically and horizontally while maintaining said table top parallel to said floor, said moving of said table top being from a rest position near said floor and most distant from said work space to a work position different from said rest position and closest to and into said work space;

cradle moving means for moving said cradle from a rest position on said table top to a position extended from said table top and into said work space;

wherein said table top lifing means comprises a parallel link mechanism and a driving mechanism, said driving mechanism being expandable and contractable to drive said parallel link mechanism to cause concurrent vertical and horizontal movement of said table top while maintaining said table top parallel to said floor;

wherein said parallel link mechanism comprises a plurality of links of substantially the same length and spaced parallel to each other at a predetermined distance from each other, one end of each link being rotatably connected to said table to be angularly movable relative to said table without any lateral movement relative to said table, another end of each link being rotatably connected to said floor to be angularly movable relative to said floor without any lateral movement relative to said floor;

wherein said driving mechanism has one end pivotally connected to a portion of said parallel link mechanism and another end pivotally connected to said floor, whereby said driving mechanism fully contracts to move said links of said parallel link mechanism downwardly to a position closest to said floor and consequently moves said table top to said rest position most distant from said work space, and fully expands to move said one ends of said links of said parallel link mechanism upwardly to a position away from said floor, and consequently moves said table top to said work position closest to and into said work space; and wherein said cradle moving means comprises an angle detecting means for detecting the angle of said links of said parallel link mechanism with respect to said floor and for providing an output signal indicative of said angle; a control means responsive to said output signal for calculating the distance travelled by said cradle from said rest position on said table top and for providing a distance signal indicative of said travelled distance; and adjusting means responsive to said distance signal for adjusting the distance travelled by said cradle.

7. The table mechanism of claim 6, wherein said table lifting means comprises a cover mechanism comprising a plurality of plates disposed outside of said parallel link mechanism and parallel to said links and longitudinally of said table, one end of each plate being pivotally mounted on said table, another end of each plate being pivotally mounted on said floor, adjacent ones of said plates partially and laterally overlapping each other along their entire length.

8. The table mechanism of claim 7, wherein each of said plates of said cover mechanism has a protrusion of U-shaped cross section over an entire non-overlapping portion.

* * * * *